United States Patent [19]

Bell

[11] Patent Number: 4,975,826
[45] Date of Patent: Dec. 4, 1990

[54] DENTAL LIGHT HANDLE COVER

[76] Inventor: Valerie R. Bell, Post Office Box 529, Zoar, Ohio 44697

[21] Appl. No.: 273,485

[22] Filed: Nov. 21, 1988

[51] Int. Cl.$^5$ ............................................. F21V 15/00
[52] U.S. Cl. .................................... 362/376; 362/109; 362/804
[58] Field of Search ............... 362/109, 399, 400, 804, 362/376; 33/29; 16/110 R, 111 R, 114 R, 116 R, DIG. 12, DIG. 18; 74/558.5; 150/154, 155

[56] References Cited

U.S. PATENT DOCUMENTS

| | | | |
|---|---|---|---|
| 1,633,988 | 6/1927 | Jones | 150/155 |
| 2,639,521 | 5/1953 | Richettson | 16/116 R |
| 2,737,394 | 3/1956 | Abel | 150/160 |
| 4,559,671 | 12/1985 | Andrews et al. | 16/114 R |
| 4,605,124 | 8/1986 | Sandel et al. | 16/114 R |
| 4,777,574 | 10/1988 | Eisner | 362/804 |
| 4,795,669 | 1/1989 | Bowskell et al. | 362/804 |

OTHER PUBLICATIONS

AsepDent Instructional Sheet
Steri-Shield Products, Inc. Advertising Sheet.
Collection of Sundry Advertisements of Competing Products 8/88.
Infection Control Report, 5/88.

Primary Examiner—Ira S. Lazarus
Assistant Examiner—Sue Hagarman
Attorney, Agent, or Firm—Michael Sand Co.

[57] ABSTRACT

A replaceable disposable cover for a handle of a dental light in a first embodiment (10) includes a bag (12) having an interior area (22). The bag has an open first side (16). An elastic strip (24) is attached to the bag and extends around a perimeter of the bag parallel to the open side. A skirt portion (28) enables installation and removal of the cover from a T-shaped handle (32) of a first type of dental light (30) without touching the handle. In a second embodiment (50) the cover has a pair of opposed bags (52, 54) having opposed open sides (58, 64). A pair of elastic strips (70, 74) extend between the bags and are attached thereto. The elastic strips hold the cover in position on opposed rectangular handles (82, 82') of a second type of dental light (80).

17 Claims, 2 Drawing Sheets

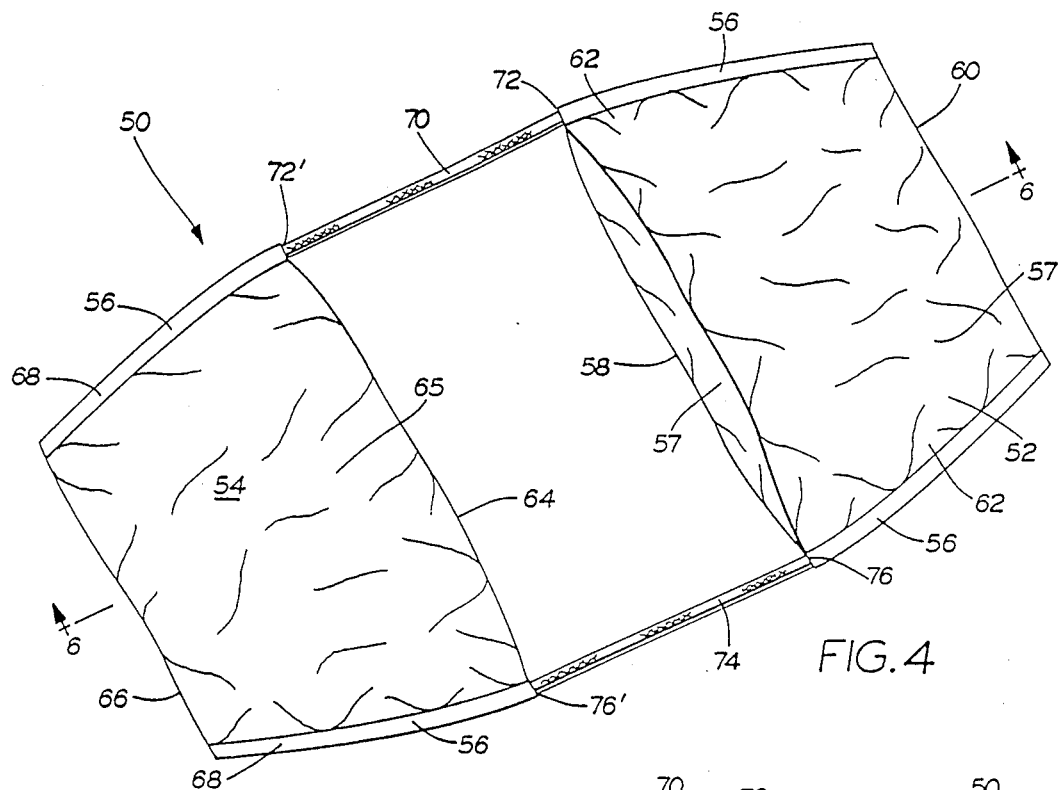

DENTAL LIGHT HANDLE COVER

BACKGROUND OF THE INVENTION

1. Technical Field

This invention relates to covers for items used during medical procedures that may be subject to contamination by bodily fluids. Particularly, this invention relates to a replaceable cover for a handle of a dental light.

2. Background Information

It is important that surfaces exposed to blood and saliva during medical procedures be decontaminated between patients to avoid the spread of disease. This need is particularly critical in view of the rapid spread of acquired immune deficiency syndrome (AIDS). The U.S. Public Health Service/Center for Disease Control and the American Dental Association both have issued guidelines for procedures designed to prevent cross-contamination and the spread of disease between patients.

During dental procedures dental lights may be exposed to a patient's blood or saliva. It is also necessary for the doctor or clinician to move the dental light to various positions during dental procedures. As the doctor or clinician touches the light, the handles may become contaminated with bodily fluid. If the handles are not disinfected, this contamination may be transmitted to subsequent patients by the repeated touching of the light handles. To avoid having to disinfect the light handles between patients, devices have been developed which can be used to cover the light handles and then removed or replaced. Lorvic Corporation, for example, has developed a product it calls "EZ Guard" which is a plastic sheet intended to be wrapped around the handles of a dental light. The plastic which is similar to household plastic, clings to the handle. Aluminum foil sheets made by Practicon, Inc. are designed to be similarly used. The problem with these handle covers is that they do not cover the entire handle and are often difficult to install or remove. It is also necessary to touch the handle to install or remove these covers. This presents the possibility of contamination. The covers may also come off during a dental procedure as the result of frequent movement of the light by the doctor or clinician.

Another cover known in the prior art is produced by Asepdent. It is a small plastic bag that can be either wrapped around the handle of the dental light in the same manner as a sheet, or can be pulled over the handle. This cover has the same drawbacks as the sheet covers. Steri-Shield Products, Inc. produces a glove-like latex cover for dental light handles. This product is difficult to install and remove, and is relatively expensive.

Northwest Dental, Inc. markets a molded plastic cover that is folded in half in "clam shell" fashion to cover a T-shaped dental light handle. This device once in place is secure but it is difficult to apply and lock in place. Also it is relatively expensive to produce in comparison to the other known devices.

Thus, there exists a need for a dental light handle cover that is easy to install and remove. Further, there is a need for a dental light handle cover that covers the entire handle surface, and which can be installed or removed without touching the handle. There is also a need for a dental light handle cover that will not fall off the handle after it is installed or unravel during procedures. There is also a need for a dental light handle cover that is economical to produce and use.

SUMMARY OF THE INVENTION

It is an object of the present invention to provide a cover for a handle of a dental light that is easy to install and remove.

It is a further object of the present invention to provide a cover for a handle of a dental light that covers the entire handle surface.

It is a further object of the present invention to provide a cover for a handle of a dental light that can be installed and removed without touching the handle.

It is a further object of the present invention to provide a cover for a handle of a dental light that remains attached to the handle despite repeated movement.

It is a further object of the present invention to provide a cover for a handle of a dental light that is economical to produce and use.

Further objects of the present invention will be made apparent in the following Best Modes for Carrying Out the Invention and the Appended Claims.

The foregoing objects are accomplished in the preferred form of the invention by a replaceable, disposable cover for a handle of a dental light, which cover includes a flexible bag. The bag is made of polyethylene. The bag has an interior area sized for accepting the handle, and an opening through which the handle may be inserted into the interior of the bag.

An elastic strap is attached to the bag adjacent the opening. The elastic strip is expandable to enable the handle to enter the interior of the bag, and then it contracts to hold the cover securely in place. In a first embodiment of the invention which is designed for the use with dental lights such as those made by Pelton Crane which have "T-shaped" handles, the bag is generally rectangular and has a first-open side. The elastic strip is disposed from the first-open side and extends about a perimeter of the bag. A skirt portion between the open side and the elastic strip is used to grasp the cover and install or remove it from the handle. This avoids having to touch the handle during these operations.

In a second embodiment of the invention used with lights such as those made by the Ritter Company which have opposed rectangular handles, the cover includes a first bag and a second bag. The bags are generally rectangular in profile and each have an open side. The open sides of the bags are positioned in an opposed fashion. A pair of elastic strips extend between the bags across the body of the light to hold the bags in position on the handles.

BRIEF DESCRIPTION OF THE DRAWINGS

Preferred embodiments of the invention illustrative of the best mode in which applicant has contemplated applying the principles, are set forth in the following description and are shown in the drawings and are particularly and distinctly pointed out and set forth in the appended claims.

FIG. 4 is a perspective view of a second embodiment of the dental light handle cover of the present invention.

FIG. 5 is a plan view of a dental light with the handle cover shown in FIG. 4 installed on its handles.

FIG. 6 is a sectioned view of the dental light handle cover shown in FIG. 4 sectioned along line 6—6.

Similar numerals refer to similar parts throughout the drawings.

DESCRIPTION OF THE PREFERRED EMBODIMENTS

Figure 1:
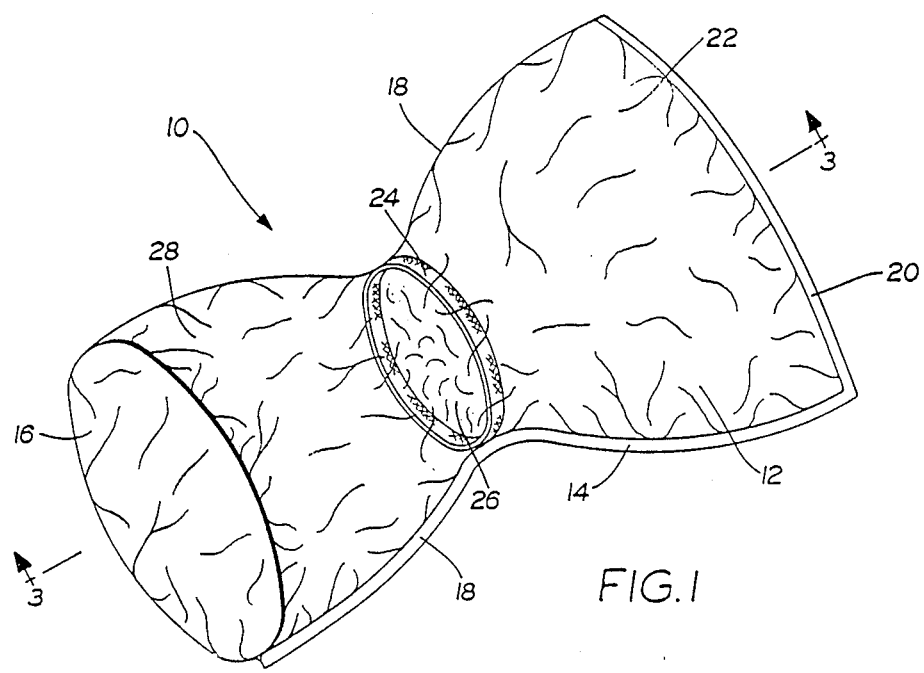
FIG. 1 is a perspective view of a first embodiment of the dental light handle cover of the present invention.

Referring now to the drawings and particularly to FIG. 1, there is shown therein a first embodiment of the dental light handle cover of the present invention generally indicated 10. The cover includes bag means 12 which in the preferred form of the invention is a polyethylene bag. The bag is generally rectangular in profile when laid flat. A first side 16 of the bag is open. The bag also has a pair of closed lateral sides 18 and a closed end 20. In the preferred form of the invention, the bag is economically formed of a plastic sheet folded over on itself and sealed along two sides at a seam 14.

The bag has an interior area 22 that is surrounded by the bag on three sides. An elastic strip 24 extends around a perimeter of the bag parallel to the first side. The elastic strip is attached to the bag by either sewing, heat sealing or an adhesive. Elastic strip 24 serves as elastic means and is expandable and contractible. The elastic strip 24 defines an opening 26 to interior area 22 of the bag.

The bag also includes a skirt portion 28. Skirt portion 28 is the area of the bag between elastic strip 24 and first side 16.

Figure 2:
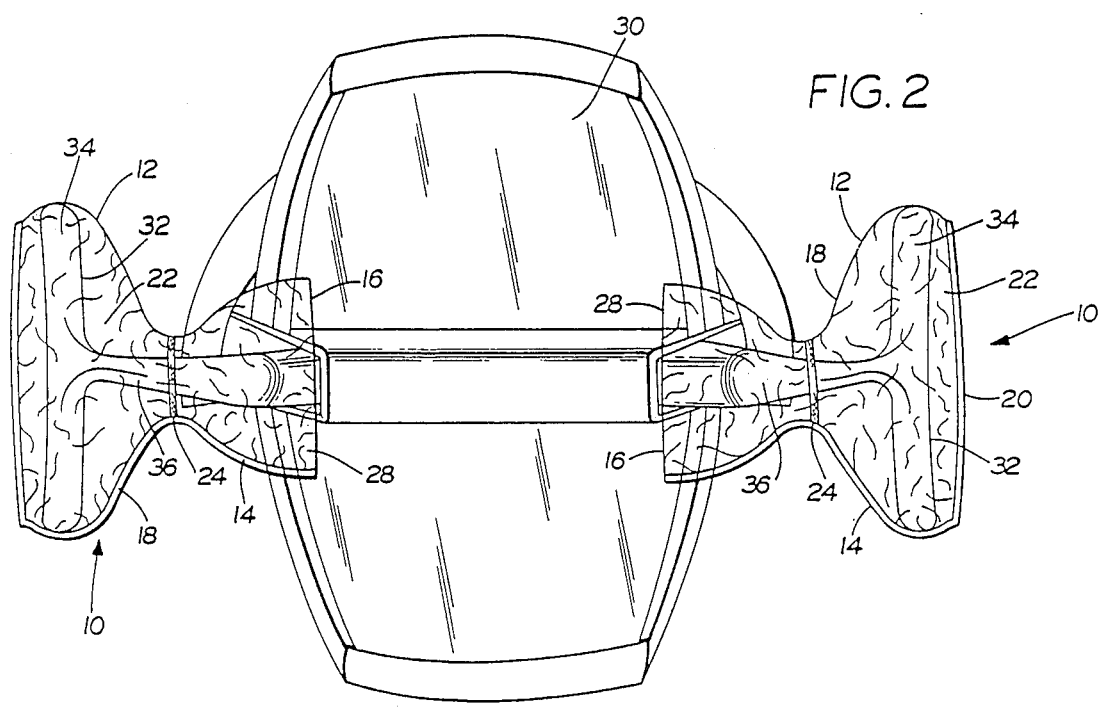
FIG. 2 is a plan view of a dental light with two of the handle covers shown in FIG. 1 installed on its handles.
Figure 3:
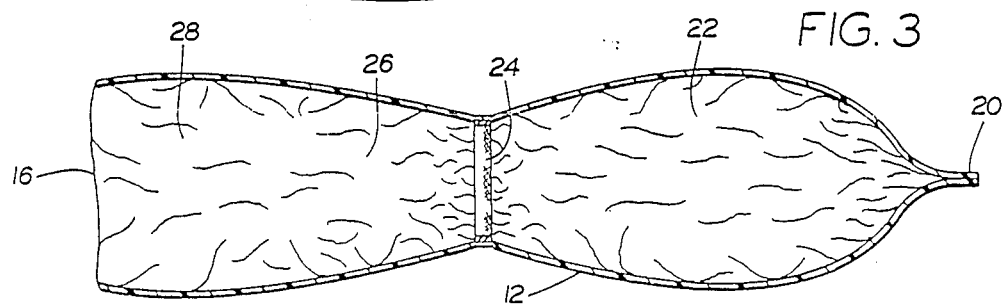
FIG. 3 is a view of the handle cover shown in FIG. 1 sectioned along line 3—3.

Cover 10 is shown installed on a dental light 30 in FIG. 2. Light 30 is of the type made by Pelton Crane which has a pair of "T-shaped" handles 32. Each T-shaped handle 32 includes a head portion 34 and a post portion 36. Cover 10 is installed on handle 32 by inserting head portion 34 of the handle into the bag through first side 16. The elastic strip 24 is expanded so head portion 34 enters the interior area 22 through opening 26. Once the bag is over the head portion of the handle, elastic strip 24 contracts on post portion 36 to hold the cover on the handle. Skirt portion 28 covers the entire post portion 36 of the handle up to where the post portion joins the main body of the light.

Although in other embodiments, the cover may be made without a skirt portion 28 and terminate at elastic strip 24, the skirt portion provides several advantages. First, it serves as tab means to pull and manipulate the cover over the handle without holding or touching the handle itself. This lowers the probability of contamination. It also serves to cover the entire handle to avoid contamination in areas where the handle might be touched infrequently. It will be understood by those skilled in the art that in other embodiments of the invention the tab means could be one or more flaps or strips.

A second embodiment of the invention generally indicated 50 is shown in FIG. 4. The second embodiment is designed for use with dental lights made by the Ritter Company or others, which have dual opposed, rectangular handles. Cover 50 includes a first bag 52 and a second bag 54 both of which serve as bag means. Bags 52 and 54 are generally rectangular in profile, and in the preferred form each is made from a single polyethylene sheet sealed at two seams 56. First bag 52 has a first side 58 which is open and an opposed closed side 60. Bag 52 also includes a pair of closed lateral sides 62 which correspond to the seams 56 of the first bag. Bag 52 also has an interior area 57.

Second bag 54 has a second open side 64 opposed of first side 58 of first bag 52. Second bag 54 also has a closed side 66 opposite second open side 64 and a pair of lateral sides 68 similar to seams 56 of bag 54. Bag 54 also has an interior area 65.

A first elastic strap 70 extends between a first end 72 of bag 52 and a first end 72' of bag 54. A second elastic strip 74 extends between a second end 76 of bag 52, and a second end 76' of bag 54.

Elastic strips 70 and 74 serve as elastic means and are expandable and contractible. They are attached to the first and second bags by either sewing, heat sealing or an adhesive. The elastic strips are preferably attached to seams 56 which provide additional strength.

A dental light 80 with cover 50 installed is shown in FIG. 5. Light 80 is of the type made by Ritter which has opposed rectangular handles 82 and 82'. When cover 50 is installed, handle 82 is inserted into interior area of 57 of bag 52 through an opening formed by first open side 58. Handle 82' is inserted into the interior area 65 of bag 54 through an opening formed by second open side 64. Elastic strips 70 and 74 are intially expanded to enable the handles to fit into the bags, and thereafter contract to hold cover 50 firmly in place on the handles.

In the case of dental light 80 and similarly styled lights, cover 50 may be readily installed without touching the handles. Thus, there is no need for a skirt portion or similar structure in the second embodiment as is desirable in the first embodiment.

It will be understood by those skilled in the art that the invention may be modified to suit other types of light configurations. For example, the elastic strips in the second embodiment could be replaced by a single strip of elastic material. The size and shape of the bag means could also be changed to enable the cover to be fit over other types of handles or devices.

Thus, the new cover for a handle of a dental light achieves the above stated objectives, eliminates dificulties enountered in prior devices, solves problems, and obtains the desirable results described herein.

In the foregoing description, certain terms have been used for brevity, clarity and understanding. However, no unnecesary limitations are to be implied therefrom because such terms are for descriptive purposes and are intended to be broadly construed. Moreover, the description and illustrations given are by way of example, and the invention is not limited to the exact details shown or described.

Having the described the features, discoveries, and principles of the invention, the manner in which it is constructed and used and the advantages and useful results obtained, the new and useful structures, devices, elements, arrangements, parts, combinations, systems, equipment, operations, and relationships are set forth in the appended claims.

I claim:

1. A replaceable disposable cover for covering handle means of a medical apparatus, comprising:
    (a) flat bag means generally rectangular in profile and formed of plastic for accepting said handle means, said bag means having an interior area and an opening formed in a first side of said bag means sized for accepting the handle means, said interior area and opening being sized for slideably receiving said handle means into the interior area without stretching and deforming of the bag means; and
    (b) elastic means comprising at least a single strip of elastic material secured to the bag means adjacent the opening for securing the bag means on the handle means.

2. The cover according the claim 1 wherein the bag means is a single bag and said handle means is a "T-shaped" handle and wherein said elastic strip extends about a perimeter of said bag, said perimeter generally parallel and adjacent said opening.

3. The cover according to claim 2 and further comprising tab means for holding said bag, wherevy said cover may be installed and removed without touching said handle.

4. The cover according to claim 1 wherein said handle means are first and second handles in opposed positions on said apparatus and said bag means comprises a first bag and a second bag, said first and second bags generally rectangular in profile, whereby when said cover is installed, said first handle is inserted into the interior area of first bag and said second handle is inserted into the interior area of said second bag.

5. The cover according to claim 1 wherein said elastic means comprises a pair of elastic strips extending between said first and second bags.

6. The cover according to claim 5 wherein said first bag includes an opening along a first side of said first bag and the second bag includes an opening along a second side of said second bag, said first and second sides opposed.

7. The cover according to claim 5 wherein said handle means are opposed rectangular handles and said apparatus is a dental light.

8. The cover according to claim 7 wherein said elastic strips are attached to said bags by heat sealing.

9. The cover according to claim 7 wherein said elastic strips are attached to said bags by sewing.

10. The cover according to claim 7 wherein said elastic strips are attached to said bags with an adhesive.

11. A replaceable disposable cover for covering a T-shaped handle of a medical apparatus, comprising:
  (a) a flexible bag for accepting said handle, said bag being generally rectangular in profile and having an interior area and an opening formed in a first side of said bag, said interior area and opening sized for accepting said handle;
  (b) elastic means adjacent said opening, said elastic means comprising a strip of elastic material extending about a perimeter of the bag generally parallel and adjacent said opening and attached to said bag by attaching means, said elastic strip being expandable to enable said handle to be inserted into the interior area of said bag, and thereafter contractible to hold said handle in said interior area; and
  (c) tab means for holding said bag, whereby the cover may be installed and removed without touching the handle.

12. The cover according to claim 11 wherein said tab means is a skirt portion of said bag and wherein said elastic strip is disposed of said first side and said skirt portion defined by said elastic strip and said open side.

13. The cover according to claim 12 wherein said bag is made of polyethylene plastic.

14. The cover according to claim 13 wherein said medical apparatus is a dental light.

15. The cover according to claim 14 wherein the elastic strip is attached to said bag by heat sealing.

16. The cover according to claim 14 wherein the elastic strip is attached to said bag by sewing.

17. The cover according to claim 14 wherein said elastic strip is attached to said bag by an adhesive.

* * * * *